(12) United States Patent
Bender et al.

(10) Patent No.: US 9,945,679 B2
(45) Date of Patent: Apr. 17, 2018

(54) PERSONALIZED TRAVEL ROUTES TO REDUCE STRESS

(71) Applicant: International Business Machines Corporation, Armonk, NY (US)

(72) Inventors: Michael Bender, Rye Brook, NY (US); Rhonda L. Childress, Austin, TX (US); Michael P. Shute, Niantic, CT (US)

(73) Assignee: International Business Machines Corporation, Armonk, NY (US)

( * ) Notice: Subject to any disclaimer, the term of this patent is extended or adjusted under 35 U.S.C. 154(b) by 30 days.

(21) Appl. No.: 15/193,299

(22) Filed: Jun. 27, 2016

(65) Prior Publication Data
US 2017/0370732 A1 Dec. 28, 2017

(51) Int. Cl.
*G01C 21/34* (2006.01)
*G05D 1/00* (2006.01)
*A61B 5/18* (2006.01)
*G08G 1/0968* (2006.01)

(52) U.S. Cl.
CPC ........... *G01C 21/34* (2013.01); *G05D 1/0088* (2013.01); *A61B 5/18* (2013.01); *G01C 21/3453* (2013.01); *G01C 21/3461* (2013.01); *G01C 21/3484* (2013.01); *G08G 1/096838* (2013.01)

(58) Field of Classification Search
CPC  G01C 21/34; G01C 21/3453; G01C 21/3461; G01C 21/3484; A61B 5/18; G08G 1/096838; G05D 1/0088
See application file for complete search history.

(56) References Cited

U.S. PATENT DOCUMENTS

| 7,610,151 | B2 | 10/2009 | Letchner et al. |
| 8,126,641 | B2 | 2/2012 | Horvitz |
| 8,509,826 | B2 | 8/2013 | Karmarkar et al. |
| 9,618,359 | B2 * | 4/2017 | Weast ............... G01C 21/3697 |

(Continued)

OTHER PUBLICATIONS

P. Mell et al., "The NIST Definition of Cloud Computing", National Institute of Standards and Technology, Information Technology Laboratory, Sep. 2011, pp. 1-7.

(Continued)

*Primary Examiner* — Todd Melton
(74) *Attorney, Agent, or Firm* — Law Office of Jim Boice

(57) ABSTRACT

One or more processors identify an occupant of a passenger vehicle, and then receive biometric sensor readings from a biometric sensor that is monitoring the occupant in real time, where the biometric sensor readings indicate a real-time emotional state of the occupant. The processor(s) generate a personal profile for the occupant of the passenger vehicle based on the biometric sensor readings. The processor(s) receive a desired destination and travel schedule for the occupant of the passenger vehicle, as well as environmental sensor readings indicating a real-time environmental state of the passenger vehicle. The processor(s) then create a travel route for the passenger vehicle based on the biometric sensor readings, the personal profile of the vehicle occupant, the desired destination and travel schedule, and the real-time environmental state of the passenger vehicle. One or more processors then transmit, to the passenger vehicle, directions for the travel route.

20 Claims, 7 Drawing Sheets

(56) References Cited

U.S. PATENT DOCUMENTS

| | | | |
|---|---|---|---|
| 9,733,097 B2* | 8/2017 | Sisbot | G01C 21/3461 |
| 9,766,084 B2* | 9/2017 | Kim | G01C 21/3407 |
| 2008/0004884 A1 | 1/2008 | Flake et al. | |
| 2014/0236414 A1 | 8/2014 | Droz et al. | |
| 2016/0089954 A1* | 3/2016 | Rojas Villanueva | G01C 21/3484 701/36 |
| 2017/0191838 A1* | 7/2017 | Laur | G01C 21/34 |

OTHER PUBLICATIONS

Ferscha et al., "Wearable Displays for Everyone!" Pervasive Computing, IEEE 9.1 (2010): 7-10.
Guede Fernandez et al., "Using Smartphone Bases Biodevices for Analyzing Physiological, Psychological and Behavioral User's Habits", Proceedings of the 6th International Conference on Biomedical Electronics and Devices, Scitepress, 2013, pp. 243-248.
Khan et al., "Mobile Phone Sensing Systems: A Survey", IEEE Communications Surveys Tutorials, 15.1 (2013): 402-427.
Mohan et al., "Trafficsense: Rich Monitoring of Road and Traffic Conditions Using Mobile Smartphones", Proceedings of the 6th ACM Conference on Embedded Network Sensor Systems, ACM, 2008, pp. 1-29.
A. Brown, "Wearables for Mental Health", www.wearable-technologies.com, Sep. 17, 2015, pp. 1-5.
Spire, Inc., "Spire", Spire, Inc., www.spire.io, Retrieved Jun. 27, 2016, pp. 1-10.
V. Patil et al., "Voice Stress Detection", International Journal of Electrical, Electronics, and Computer Engineering, 2(2): 148-154 (2013).
Olive Labs, Inc., "A Stylish, Intelligent Wearable Band That Helps You Conquer Stress", Olive Labs, Inc., www.indiegogo.com/projects/olive-a-wearable-to-manage-stress#/, retrieved Jun. 27, 2016, pp. 1-19.
F. Baronti, "Distributed Sensor for Steering Wheel Rip Force Measurement in Driver Fatigue Detection", Design, Automation & Test in Europe Conference & Exhibition, IEEE, 2009, pp. 894-897 (Abstract Only).
N. Oran, "Sharecare Is Measuring Stress Levels With Voice Recognition Tech to Improve Health (and to Get Insight on the Presidential Debates)", medcitynews.com, Breaking Media, Inc., Jan. 15, 2016, pp. 1-6.
IBM, "Tone Analyzer", IBM, www.ibm.com, 2016, pp. 1-3.
IBM, "Speech to Text", IBM, www.ibm.com, 2016, pp. 1-4.
IBM, "Tradeoff Analytics", IBM, www.ibm.com, 2016, pp. 1-4.
IBM, "Analytics Made Easy", IBM, www.ibm.com, Retrieved Jun. 27, 2016, pp. 1-3.

* cited by examiner

PERSONALIZED TRAVEL ROUTES TO REDUCE STRESS

BACKGROUND

The present disclosure relates to the field of vehicles, and specifically to the field of vehicles that transport passengers. Still more specifically, the present disclosure relates to the field of controlling the operation of a passenger vehicle based on a stress level of one or more occupants of the passenger vehicle.

SUMMARY

In accordance with one or more embodiments of the present invention, a method, system, and/or computer program product establish a travel route for a passenger vehicle based on a real-time emotional state of an occupant of the passenger vehicle. One or more processors identify an occupant of a passenger vehicle. One or more processors receive biometric sensor readings from a biometric sensor that is monitoring the occupant in real time, where the biometric sensor readings indicate a real-time emotional state of the occupant. One or more processors generate a personal profile for the occupant of the passenger vehicle based on the biometric sensor readings received from the biometric sensor that is monitoring the occupant in real time. One or more processors receive a desired destination and travel schedule for the occupant of the passenger vehicle. One or more processors receive environmental sensor readings indicating a real-time environmental state of the passenger vehicle. One or more processors create a travel route for the passenger vehicle based on the biometric sensor readings, the personal profile for the occupant of the passenger vehicle, the desired destination and travel schedule, and the real-time environmental state of the passenger vehicle. One or more processors then transmit, to the passenger vehicle, directions for the travel route.

DETAILED DESCRIPTION

Figure 1:
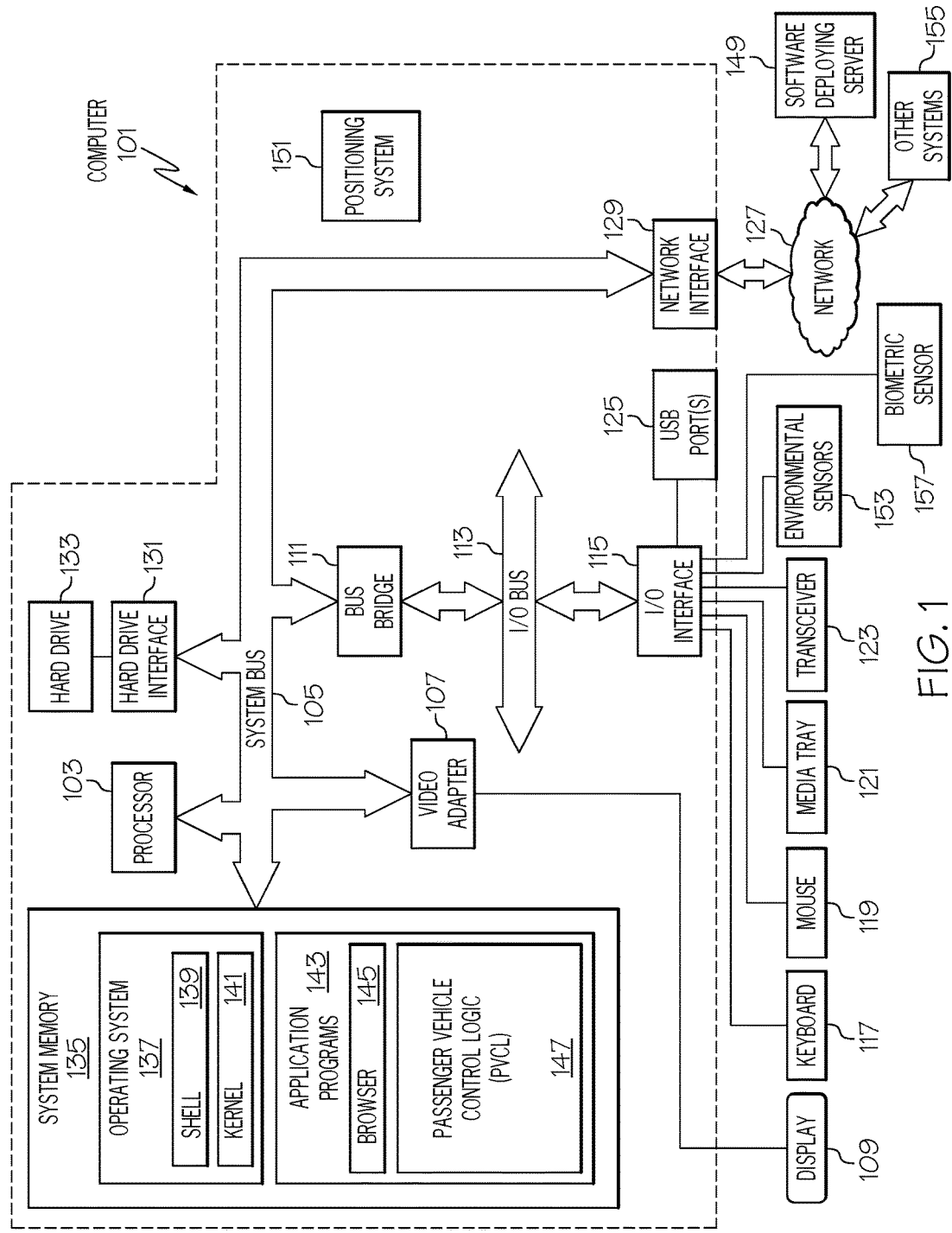
FIG. 1 depicts an exemplary system and network in which the present disclosure may be implemented.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

With reference now to the figures, and in particular to FIG. 1, there is depicted a block diagram of an exemplary system and network that may be utilized by and/or in the implementation of the present invention. Some or all of the exemplary architecture, including both depicted hardware and software, shown for and within computer 101 may be utilized by software deploying server 149 and/or other systems 155 shown in FIG. 1, and/or vehicle support system 201 and/or electronic device 255 shown in FIG. 2, and/or a self-driving vehicle (SDV) on-board computer 501 shown in FIG. 5.

Exemplary computer 101 includes a processor 103 that is coupled to a system bus 105. Processor 103 may utilize one or more processors, each of which has one or more processor cores. A video adapter 107, which drives/supports a display 109, is also coupled to system bus 105. System bus 105 is coupled via a bus bridge 111 to an input/output (I/O) bus 113. An I/O interface 115 is coupled to I/O bus 113. I/O interface 115 affords communication with various I/O devices, including a keyboard 117, a mouse 119, a media tray 121 (which may include storage devices such as CD-ROM drives, multi-media interfaces, etc.), a transceiver 123 (capable of transmitting and/or receiving electronic communication signals), and external USB port(s) 125. While the format of the ports connected to I/O interface 115 may be any known to those skilled in the art of computer architecture, in one embodiment some or all of these ports are universal serial bus (USB) ports.

As depicted, computer 101 is able to communicate with a software deploying server 149 and/or other systems 155 (e.g., establishing communication among SDV 502, vehicle support system 201, etc. as described and depicted in the figures herein) using a network interface 129. Network interface 129 is a hardware network interface, such as a network interface card (NIC), etc. Network 127 may be an external network such as the Internet, or an internal network such as an Ethernet or a virtual private network (VPN). In one or more embodiments, network 127 is a wireless network, such as a Wi-Fi network, a cellular network, etc.

A hard drive interface 131 is also coupled to system bus 105. Hard drive interface 131 interfaces with a hard drive 133. In one embodiment, hard drive 133 populates a system memory 135, which is also coupled to system bus 105. System memory is defined as a lowest level of volatile memory in computer 101. This volatile memory includes additional higher levels of volatile memory (not shown), including, but not limited to, cache memory, registers and buffers. Data that populates system memory 135 includes computer 101's operating system (OS) 137 and application programs 143.

OS 137 includes a shell 139, for providing transparent user access to resources such as application programs 143. Generally, shell 139 is a program that provides an interpreter and an interface between the user and the operating system. More specifically, shell 139 executes commands that are entered into a command line user interface or from a file. Thus, shell 139, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 141) for processing. While shell 139 is a text-based, line-oriented user interface, the present invention will equally well support other user interface modes, such as graphical, voice, gestural, etc.

As depicted, OS 137 also includes kernel 141, which includes lower levels of functionality for OS 137, including providing essential services required by other parts of OS 137 and application programs 143, including memory management, process and task management, disk management, and mouse and keyboard management.

Application programs 143 include a renderer, shown in exemplary manner as a browser 145. Browser 145 includes program modules and instructions enabling a world wide web (WWW) client (i.e., computer 101) to send and receive network messages to the Internet using hypertext transfer protocol (HTTP) messaging, thus enabling communication with software deploying server 149 and other systems.

Application programs 143 in computer 101's system memory (as well as software deploying server 149's system memory) also include Passenger Vehicle Control Logic (PVCL) 147. PVCL 147 includes code for implementing the processes described below, including those described in FIGS. 2-4. In one embodiment, computer 101 is able to download PVCL 147 from software deploying server 149, including in an on-demand basis, wherein the code in PVCL 147 is not downloaded until needed for execution. In one embodiment of the present invention, software deploying server 149 performs all of the functions associated with the present invention (including execution of PVCL 147), thus freeing computer 101 from having to use its own internal computing resources to execute PVCL 147.

Also within computer 101 is a positioning system 151, which determines a real-time current location of computer 101 (particularly when part of a self-driving vehicle as described herein). Positioning system 151 may be a combination of accelerometers, speedometers, etc., or it may be a global positioning system (GPS) that utilizes space-based satellites to provide triangulated signals used to determine two-dimensional or three-dimensional locations.

Also associated with computer 101 are environmental sensors 153, which detect an environment of the computer 101. More specifically, environmental sensors 153 are able to detect vehicles, road obstructions, pavement, etc., when implemented in a passenger or similar land-based vehicle. For example, if computer 101 is on board a vehicle, including but not limited to a self-driving vehicle (SDV) (e.g., SDV on-board computer 501 shown in FIG. 5), then environmental sensors 153 may be cameras, radar transceivers, etc. that allow the SDV to detect the environment (e.g., road obstructions, pavement, conditions, etc.) of that SDV, thus enabling it to be autonomously self-driven. Similarly, environmental sensors 153 may be cameras, thermometers, moisture detectors, etc. that detect ambient weather conditions and other environmental conditions of a roadway upon which the vehicle/SDV is traveling, as well as conditions of passengers being transported by such vehicles/SDVs.

Computer 101 is also able to communicate (via I/O interface 115 and/or via network 127) with one or more biometric sensors, including but not limited to the depicted biometric sensor 157. Biometric sensor 157 is a sensor that is able to detect biometric states of a person. Examples of such states include, but are not limited to, a person sweating (detected by a biometric sensor that is able to detect a change in galvanic skin resistance), a person's heart rhythm (e.g., as provided by biometric sensor 157 being an external electrocardiograph (ECG/EKG) monitor), a person's respiration level (e.g., as provided by biometric sensor 157 being a breathing monitor), a person's breath (e.g., as provided by biometric sensor 157 being a breathalyzer that is able to analyze the chemical content of a person's breath to indicate certain cognitive and/or physical states), etc.

The hardware elements depicted in computer 101 are not intended to be exhaustive, but rather are representative to highlight essential components required by the present invention. For instance, computer 101 may include alternate memory storage devices such as magnetic cassettes, digital versatile disks (DVDs), Bernoulli cartridges, and the like. These and other variations are intended to be within the spirit and scope of the present invention.

Current electronic mapping programs are able to estimate the time it takes for a vehicle to get from point A to point B, based on distance, current traffic conditions, etc. However, such electronic mapping programs do not take into account a person's sense of urgency for being on time for an event, how aggressive the driver is, the personality of the driver, etc. In addition, when meeting someone at a location, such programs do not take into account how prompt the person being met is (historically). Thus, the present invention provides an improvement over the prior art by providing an individual recommended leave time for a person to get to their desired location based on the aforementioned traits.

In one or more embodiments, the present invention leverages multiple inputs that are stored in a database in regards to individual drivers, in order to create personalized recommendations and directions for arriving at an event within the appropriate time buffer (while accounting for a person's risk tolerance, how stressed that person (or any passenger in the vehicle) may become due to driving conditions, the nature of the meeting at the destination, the historical punctuality of a person being met, etc.).

In one or more embodiments of the present invention, when creating an optimal travel route for a user, the system receives an input from sensors (and/or from the person's own subjective input into an electronic device such as a smart phone) that indicate a current (real-time) stress level that an individual driver (or vehicle passenger) feels. These stress levels may be caused by being stuck in traffic, being potentially late to a meeting, and/or other (unrelated) issues such as being ill, upset over other non-traffic related issues, etc. In one or more embodiments of the present invention, this information is originally entered into a profile, but is supplemented by real experience based on an Internet of Things (IoT) wearable sensors, which update the profile over time. For example, sensors in a car steering wheel can pick up signs of stress (e.g., holding wheel tighter, increased blood pressure, change in vocal tones when speaking, etc.).

Another factor that the system considers (in one or more embodiments of the present invention) when generating the optimal route includes identifying the risk of being late. That is, getting to a hospital late probably has more significant consequences than getting to the grocery store late.

Another factor that the system considers (in one or more embodiments of the present invention) when generating the optimal route includes comparing the average time an individual takes on a proposed route compared to an original estimate for a particular driver. That is, a driving profile for the particular driver and/or traffic conditions and/or weather conditions and/or amount of ambient light (e.g., sunlight) and/or amount of artificial light (e.g., from streetlights) will affect the estimated time to reach a destination. For example, if the driver profile shows that the driver consistently stays well below the speed limit regardless of traffic conditions, then the estimated arrival time will be later than that of an "average" driver.

Another factor that the system considers (in one or more embodiments of the present invention) when generating the optimal route includes comparing the average speed of the driver over time (e.g., based on historical driving data for that driver) compared to all other drivers on the same road. That is, besides evaluating the driving speed pattern for all roads (as described above), the system will evaluate a particular driver's driving history on a particular roadway and calculate that difference for different traffic conditions and/or weather conditions and/or amount of ambient light.

Another factor that the system considers (in one or more embodiments of the present invention) when generating the optimal route includes an average frequency and length of rest stops for a particular driver and/or passengers in the vehicle, calculated by a length of the route to be taken, the time of day, and the distance to the next rest stop. That is, these rest stops will lengthen the calculated/estimated time it will take a vehicle to reach its planned destination.

Another factor that the system considers (in one or more embodiments of the present invention) when generating the optimal route involves the determination of the standard deviation of predicted versus actual driving times for individual routes or components of routes. By quantifying the risk for a given route, the system can manage the risk to the tolerance and recommend personalized route selection.

Another factor that the system considers (in one or more embodiments of the present invention) when generating the optimal route involves identifying trade-offs the driver will take on speed versus being stuck in traffic and/or driving in different weather conditions and/or driving in different amounts of ambient light (e.g., sunlight). That is, many drivers prefer driving a bit longer as long as they "are moving". This information will be used to calculate alternative routes.

Another factor that the system considers (in one or more embodiments of the present invention) when generating the optimal route is to track the timeliness of a person being met at the destination (can be for either person driving to the destination) to allocate appropriate times. This history of timeliness can be determined from information found on social networking sites and/or logged in a profile by the driver.

Thus, the present invention uses cognitive computing in the integration of personal profile information, IoT sensors and historical report cards on predictions to recommend the appropriate start time for a trip, which gets a person to their target location within their personal risk tolerance while minimizing stress and learning personal habits.

The present invention gathers data on driving habits, stress, and passengers to optimize the time a person should leave to get to the destination on time with the highest probability and lowest stress based on individual personality.

In one or more embodiments, the present invention aligns the use of IoT sensors with analytics, social, mobile and cloud strategies.

The present invention thus allows a person to know when to leave for an event based on a needed arrival time, thus providing that person with the ability to utilize travel routes that the present invention has prioritized based not just on traffic, highways, tolls or other items, but also on the emotional/cognitive state (stressed, calm, hurried, etc.) of the passenger of the vehicle. In one or more embodiments of the present invention, vehicle occupant profiles are stored in an individual repository on the mobile device or in a cloud that is pertinent to an individual driver. Over time, these individual statistics will be able to modify the current recommendations based on a user's profile, which identify items such as such as roads one wishes to avoid, frequency of rest stops, and user differences when compared to the norm.

One or more embodiments of the present invention store historical predictions and actual travel times along a route to see the standard deviation of that route. As known to those skilled in the art of statistics, 68% of data values are within 1 standard deviation, 95% are within 2 and 99.7% are within 3. By knowing the standard deviation for any given route, the risk of causing increased stress to a vehicle passenger can be managed by the present invention to adjust the starting time. Such adjustments can also be based on the time of day, weather conditions, daylight/evening, etc.

As described herein, the stress level of a passenger of the vehicle can be measured with voice changes, IoT clothing checking blood pressure, or sensors checking how tight one is holding the steering wheel, etc. For example, a microphone on a user's smart phone can detect a user's voice. The smart phone can then analyze the user's voice to detect an increase in pitch, volume, etc., indicating an increased stress level of the user. Similarly, voice analysis can detect changes in stress by the vocalizations made by the user/person. Similarly, if steering wheel sensors detect that the driver is "gripping the wheel" very tightly, this is another indication of high stress levels.

Such detected stress levels can be related to traffic conditions, weather conditions, lighting, or how importance being on time is. By understanding this stress, alternative start times can be recommended to avoid bad weather, avoid traffic for a longer but steadier rate, etc.

By combining individual preferences, individual deviations from the norm, and individual handling of stress with increased statistics for any given route, a personal recommendation for leaving and/or a particular route can be provided to the user and/or the vehicle.

As described herein, one or more embodiments of the present invention utilize stress levels of vehicle occupants to create suggested travel routes, starting times, etc. These stress levels can be found in personal profile information for the passenger (e.g., a history of being anxious in heavy traffic), IoT sensors (e.g., biometric sensors in a smart phone and/or integrated into a steering wheel), and historical report cards (e.g., a driver's driving history) to make predictions as to how a vehicle occupant (driver and/or passenger) will respond to various routes, in order to recommend a particular route, the appropriate start time for a trip, etc., which gets a person to their target location within their personal risk tolerance while minimizing stress and learning personal habits.

Figure 2:
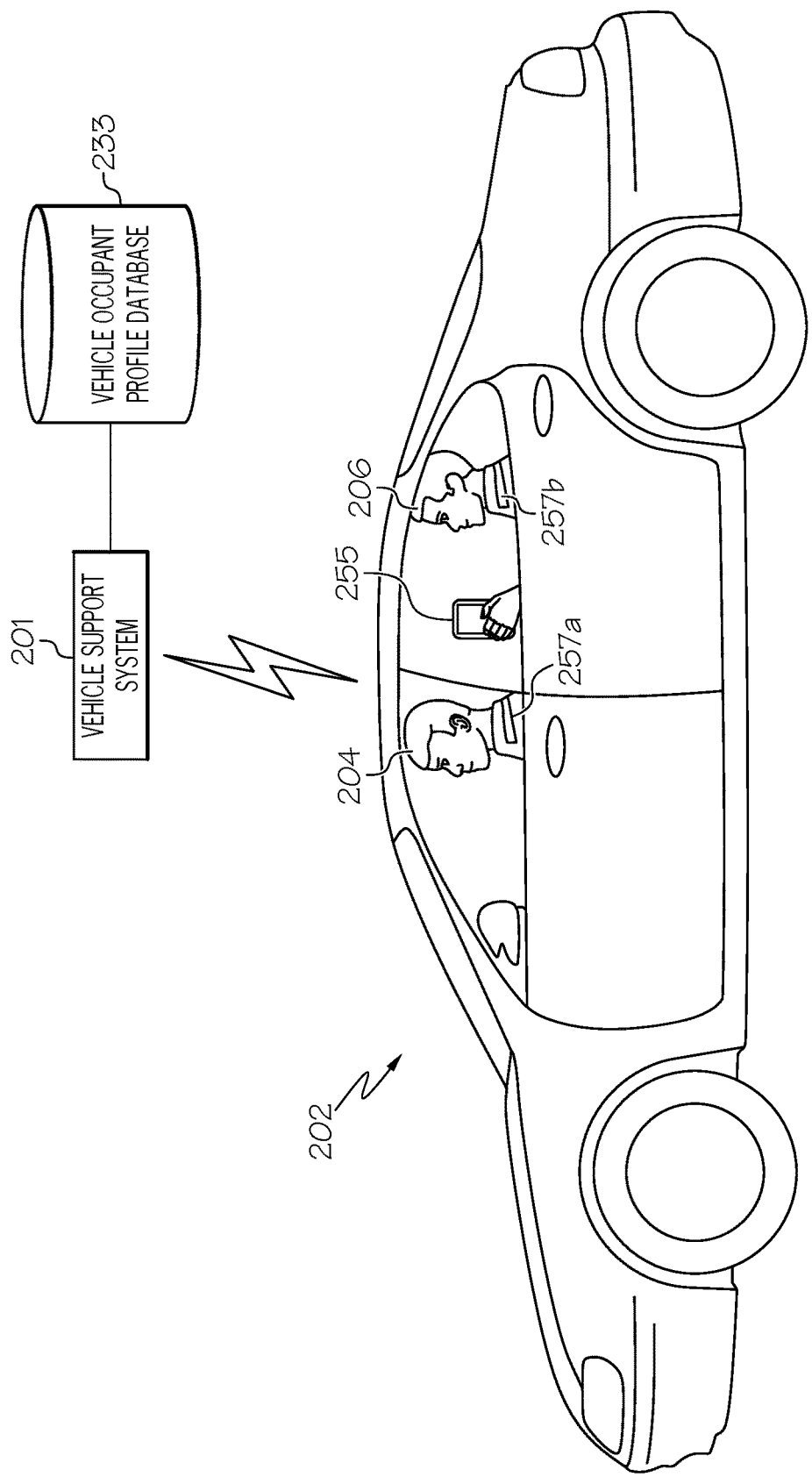
FIG. 2 illustrates an exemplary passenger vehicle transporting occupants whose emotional state is used to determine a route for the passenger vehicle.

With reference now to FIG. 2, assume that passenger vehicle 202 is transporting a driver 204 and a passenger 206. One way of measuring stress levels is the use of biometric sensors, which measure skin resistance, breath rate, ECG/EKG patterns, breath content, etc. Thus, a biometric sensor 257a (analogous to biometric sensor 157 described in FIG. 1) worn by the driver 204 will detect the stress level of the driver 204, while the biometric sensor 257b worn by passenger 206 will detect the stress level of the passenger 206. This information can be transmitted to a vehicle support system 201 (analogous to computer 101 shown in FIG. 1) for analysis.

Similarly, an electronic device 255 such as a smart phone can detect vocalizations (speech and non-speech such as yells, grunts, groans, etc.) of a vehicle occupant. These vocalizations are analyzed by logic within the electronic device 255 (e.g., by analyzing pitch, volume, speed, etc. of speech) using a Voice Stress Analysis algorithm, thus determining a current stress level of the vehicle occupant. This information can be transmitted to a vehicle support system 201, or the captured vocalizations can be sent to vehicle support system 201 for analysis therein.

Similarly, the stress level of an occupant can be determined by historical data for the occupant, as found in a vehicle occupant profile database 233 (e.g., stored in a hard drive 133 in computer 101 when configured to function as the vehicle support system 201 shown in FIG. 2). Vehicle occupant profile database 233 contains profile information about occupants of the passenger vehicle 202, including but not limited to characteristics of an aggressive driver, stress histories, changes in driving patterns due to stress of being late, etc. as differentiated from a person's normal driving patterns. While the system would be dependent on learning traits over time, the system would be primed with a user listing items that are known stress points. Those would include items such as: driving in different weather conditions, driving in different lighting conditions, are they a person that needs to be early or doesn't care if they are late, how important is moving all the time compared to sitting in traffic even if the route is faster, etc.

When presenting multiple route options to a user, tradeoff analytics can be utilized to limit the number of options presented to the user, advising the user of gains and losses to preferences that various routes present according to various user criteria, etc. In a preferred embodiment, such tradeoff analytics are performed by an intelligent cloud-based system that autonomously performs such analytics, thereby returning a level of confidence in an answer regarding a preferred route.

The above information provides a way to analyze if a person is stressed, based on what they believe to be true and what their body is showing. The present invention further adds in sensors/tracking of items that can influence a person, cognizant of the fact that stress can easily be caused by other outside influences. It is the repeated correlation of stress with a condition that increases the probability of that being a cause.

Figure 3:
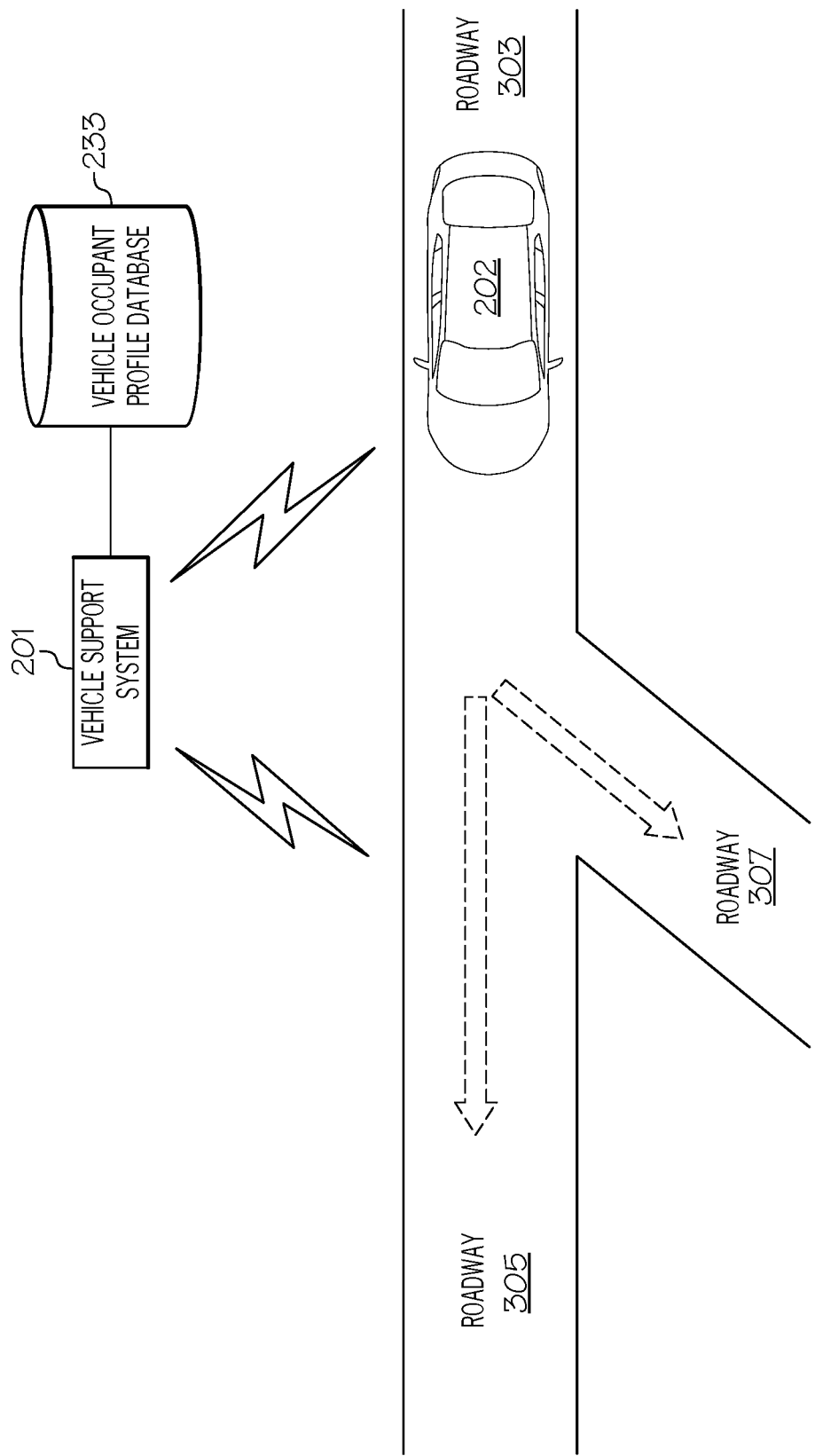
FIG. 3 illustrates alternative routes available to a passenger vehicle based on the emotional state of one or more occupants of the passenger vehicle.

In one or more embodiments of the present invention, the preferred route is established at the beginning of a trip. However, in various other embodiments the route can be dynamically adjusted. With reference to FIG. 3, assume that the passenger vehicle 202 introduced in FIG. 2 is traveling along roadway 303, and is on a route that has been previously established that includes continuing the trip by traveling along roadway 305. However, real-time biometric sensors, updated roadway conditions, etc. combined with the profile of occupants of passenger vehicle 202 (as retrieved by the vehicle support system 201 from the vehicle occupant profile database 233) are analyzed by the vehicle support system 201, thus leading to a determination as to whether the passenger vehicle 202 should proceed to roadway 305, or should alter its route in order to take roadway 307.

In one or more embodiments of the present invention, a profile is set up for individual drivers (or passengers) with the sensors or inputs described herein in order to identify stress level of the occupants of the vehicle. For each profile, the initial values may be set based on input from or on the driver (i.e., manually entered into a graphical user interface). This input allows a driver to state negative preferences such as not liking to drive on snowy days, getting stressed from being late, etc. Similarly, such profile information may include positive preferences, such as drivers stating that they do not worry if they are late; they are comfortable and competent when driving at night, etc. The system may use these as initial values, but not absolutes.

A driver is then linked to the profile, which is linked to the driver when driving a vehicle. This linkage can be via electronic handshakes (e.g. a near field communication system identifies the driver when he/she enters the car) or via a user interface (e.g., on a smart phone).

The driver enters his/her desired destination, desired time of arrival, importance of the appointment, sensors available, other passengers in the car, the average rest stops that are needed by the car occupants, etc. The appointment/target location can be entered manually or linked to a calendar of the occupant(s) of the car.

Data is then gathered from the available sensors and external sources, in order to determine weather conditions, road conditions, current traffic patterns, current vehicle speed, stress indicators (from biometric sensors), voice/vocal stress levels (using voice stress analysis), outside noise levels, external influences (radio playing, genre of content from the radio), the time of day/sunset/rush hour, etc.

The system analyzes the standard driving estimates and adjusts them based on personal responses and/or sensor readings.

The system presents the driver with the alternative routes and starting times, displays the risks for increased stress that have been identified and presents the options to the driver for leaving/route. The system will notify the driver at the appropriate time to leave and adjust as current traffic conditions change.

The system tracks stress level during the trip and identifies factors that are potential influences on the increased stress—along with a level of confidence about the future impact on an individual's stress level.

Based on desired arrival time, the system will also capture different driving patterns from the norm for an individual as an additional input of potential stress levels.

To minimize outside influences, the system displays dimensional information that was active at the times that stress was tracked, and allows the driver to mark his belief of the importance of that influence on the stress level.

The above inputs are used to update the personal profile for future trips as the system learns from an individual's history.

In an additional embodiment, the system can analyze stress even when a firm arrival time is not required. The system can also recommend changes during a trip that can reduce stress (e.g. take a short break, turn on/off radio or change station).

Figure 4:
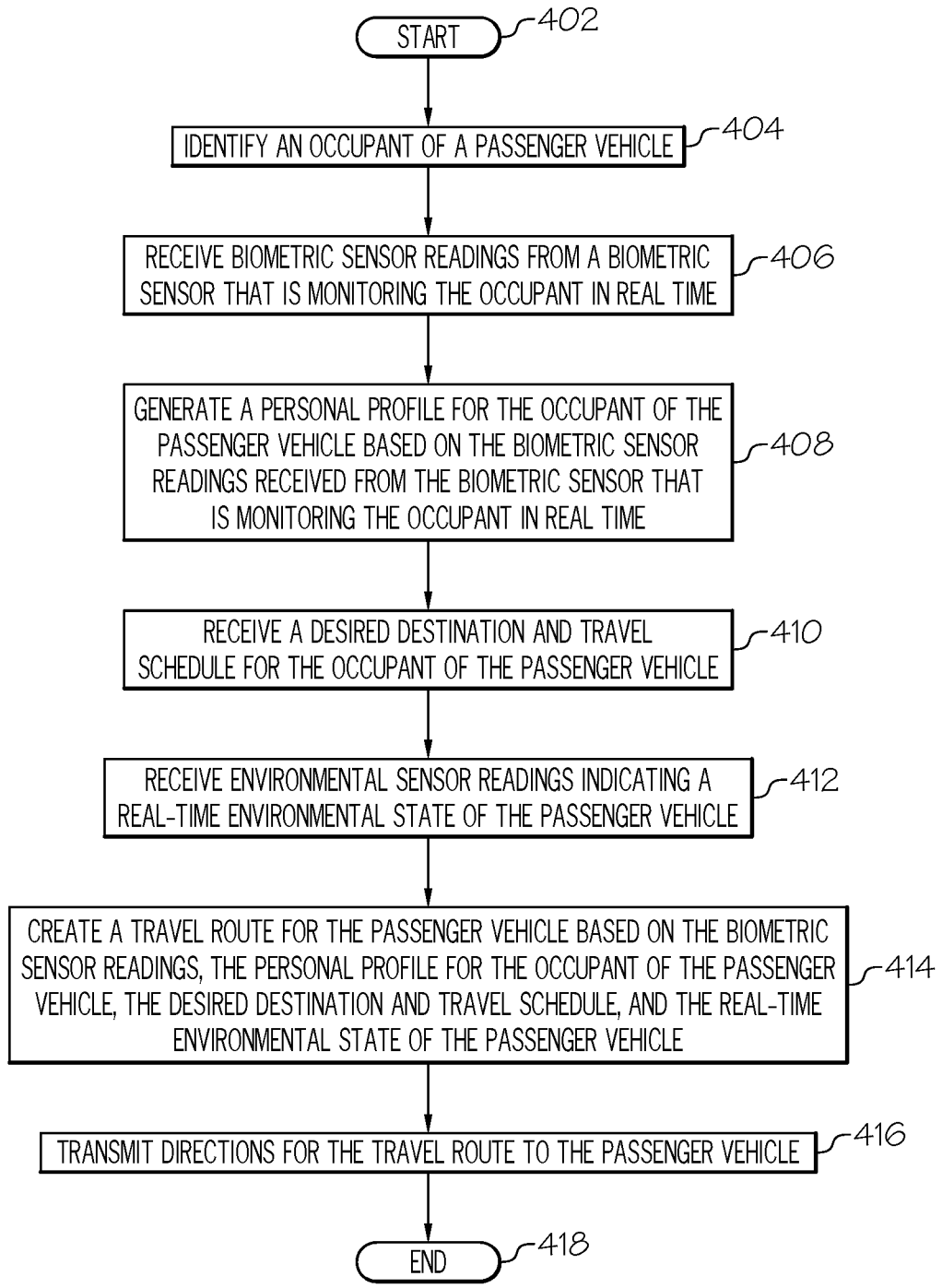
FIG. 4 is a high-level flow chart of one or more steps performed by one or more processors and/or other hardware devices to identify a preferred route for and/or to control operations of a passenger vehicle based on an emotional state of one or more occupants of the passenger vehicle in accordance with one or more embodiments of the present invention.

With reference now to FIG. 4, a high-level flow chart of one or more steps performed by one or more processors and/or other hardware devices to identify a preferred route for and/or to control operations of a passenger vehicle based on an emotional state of one or more occupants of the passenger vehicle in accordance with one or more embodiments of the present invention.

After initiator block 402, one or more processors (e.g., within vehicle support system 201 shown in FIG. 2) identify an occupant (e.g., driver 204 and/or passenger 206) of a passenger vehicle (e.g., passenger vehicle 202), as described in block 404.

As described in block 406, one or more processors receive biometric sensor readings from a biometric sensor (e.g., biometric sensor 257a and/or biometric sensor 257b and/or electronic device 255) that is monitoring the occupant in real time. As described herein, the biometric sensor readings indicate a real-time emotional state of the occupant (e.g., based on their skin sweating, their breath rate, their heart rate/rhythm, their voice inflection, etc.).

As described in block 408, one or more processors generate a personal profile for the occupant of the passenger vehicle based on the biometric sensor readings received from the biometric sensor that is monitoring the occupant in real time. This persona profile may be stored in a database such as the vehicle occupant profile database 233 shown in FIG. 2.

As described in block 410, one or more processors receive a desired destination and travel schedule for the occupant of the passenger vehicle. This information may be input into a graphical user interface (e.g., on the electronic device 255 depicted in FIG. 2), or may be retrieved from a calendar for the occupant(s).

As described in block 412, one or more processors receive environmental sensor readings (e.g., from environmental sensors 153 shown in FIG. 1) indicating a real-time environmental state of the passenger vehicle. These environmental sensors 153 may be mounted on the passenger vehicle 202 shown in FIG. 2, or they may be located along any of the roadways (303, 305, 307) shown in FIG. 3.

As described in block 414, one or more processors create a travel route for the passenger vehicle based on the biometric sensor readings, the personal profile for the occupant of the passenger vehicle, the desired destination and travel schedule, and the real-time environmental state of the passenger vehicle.

As described in block 416, one or more processors (and/or a transmitter such as transceiver 123 shown in FIG. 1 when incorporated into the vehicle support system 201 shown in FIG. 2) then transmit, to the passenger vehicle, directions for the travel route (e.g., on a display in the cabin of the passenger vehicle).

The flow-chart ends at terminator block 418

In an embodiment of the present invention, the desired destination for the occupant of the passenger vehicle is for an appointment for the occupant. In this embodiment, the method further includes receiving, by one or more processors, an indication of an importance level of the appointment for the occupant. That is, a doctor's appointment may be deemed more important than a trip to the corner grocery store. One or more processors then adjust the travel route based on the importance level of the appointment for the occupant.

In an embodiment of the present invention, one or more processors adjust the travel route based on biometric sensor readings for other occupants of the passenger vehicle. For example, assume that the original route was developed to minimize the stress level of an occupant of the passenger vehicle. However, if the driver's stress level will be greatly increased if this original route is taken, then the route may be modified, since the cognitive state of the driver has a greater impact on the safety of the passenger vehicle than that of a passenger.

In an embodiment of the present invention, the occupant is a driver of the passenger vehicle, and the method further includes retrieving, by one or more processors, a driver profile for the driver of the passenger vehicle. One or more processors then adjust the personal profile based on the retrieved driver profile to create an adjusted personal profile. One or more processors then adjust the travel route based on the adjusted personal profile of the driver of the passenger vehicle. That is, current sensor readings may indicate that the driver is stressed due to high blood pressure detected by biometric sensor 257*a*. However, the driver's profile may indicate that his/her blood pressure is normally high, and thus this high blood pressure is "normal" for that driver. As such, the current low-pressure route may not be needed for this driver, and a high-pressure route (that may be faster) will be presented to the driver.

In an embodiment of the present invention, one or more processors receive updated biometric sensor readings for the occupant while the passenger vehicle is traveling along the travel route, and then modify the travel route based on the updated biometric sensor readings. For example, assume that the planned route was for passenger vehicle 202 to be driven by driver 204 along roadway 305 shown in FIG. 3, and that roadway 305 is a high-pressure roadway (e.g., has lots of heavy traffic, winding turns, etc.), and that the initial biometric sensor readings indicated that driver 204 was in a proper state of mind to drive on roadway 305. However, while driving along roadway 303, the biometric sensors (e.g., biometric sensor 257*a* shown in FIG. 2) indicate that driver 204 has become sleepy, anxious, etc., and needs to be driving along a less stressful roadway, such as roadway 307 shown in FIG. 3. The vehicle support system 201 will then amend the planned route to take the passenger vehicle 202 onto roadway 307 in order to reach its destination.

In an embodiment of the present invention, one or more processors transmit multiple alternative routes to the occupant of the passenger vehicle (e.g., onto a display on a smart phone), thus allowing the user to select a preferred route.

While the present invention has been described herein as providing an optimal route choice to a person who is driving a vehicle, in one or more embodiments of the present invention, the vehicle is a self-driving vehicle.

Self-driving vehicles (SDVs) are vehicles that are able to autonomously drive themselves through private and/or public spaces. Using a system of sensors that detect the location and/or surroundings of the SDV, logic within or associated with the SDV controls the speed, propulsion, braking, and steering of the SDV based on the sensor-detected location and surroundings of the SDV.

Figure 5:
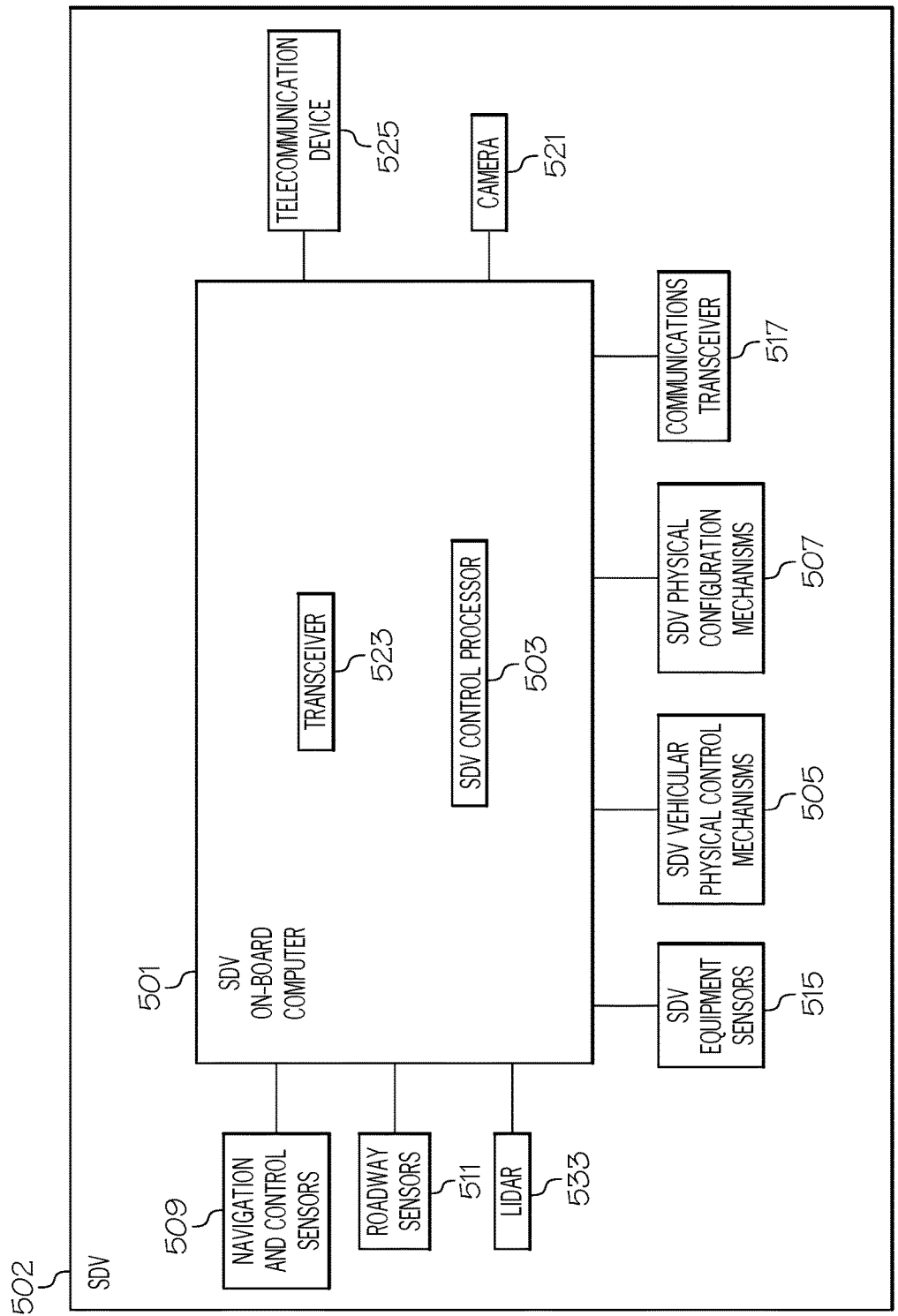
FIG. 5 depicts additional detail of hardware within an exemplary self driving vehicle (SDV) that may be utilized as a passenger vehicle in one or more embodiments of the present invention.

With reference now to FIG. 5, additional details of components within an SDV such as exemplary SDV 502 (an autonomous version of the passenger vehicle 202 shown in FIG. 2) are presented. As shown in FIG. 5, SDV 502 has an SDV on-board computer 501 that controls operations of the SDV 502. Thus, vehicle support system 201 shown in FIG. 2 is wirelessly coupled to the SDV on-board computer 501 in order to be able to control the movement and operation of SDV 502. While in autonomous mode, SDV 502 operates without the input of a human driver, such that the engine, steering mechanism, braking system, horn, signals, etc. are controlled by the SDV control processor 503, which is under the control of the SDV on-board computer 501 (based on instructions provided by vehicle support system 201). That is, by the SDV on-board computer 501 processing driving instructions received (e.g., from the vehicle support system 201 shown in FIG. 2) by a communications transceiver 517 and inputs taken from navigation and control sensors 509, then the SDV 502 is able to autonomously drive itself.

Thus, communications transceiver 517 is able to receive and transmit electronic communication signals (e.g., RF messages) from and to other communications transceivers found in other vehicles, servers, monitoring systems, etc. This enables SDV control processor 503 to autonomously control SDV vehicular physical control mechanisms 505 (e.g., the engine throttle, steering mechanisms, braking systems, turn signals, etc.) on SDV 502.

As just mentioned, the SDV on-board computer 501 uses outputs from navigation and control sensors 509 to control the SDV 502. Navigation and control sensors 509 include hardware sensors that 1) determine the location of the SDV 502; 2) sense other cars and/or obstacles and/or physical structures around SDV 502; 3) measure the speed and direction of the SDV 502; and 4) provide any other inputs needed to safely control the movement of the SDV 502.

With respect to the feature of 1) determining the location of the SDV 502, this can be achieved through the use of a positioning system such as positioning system 151 shown in FIG. 1. Positioning system 151 may use a global positioning system (GPS), which uses space-based satellites that provide positioning signals that are triangulated by a GPS receiver to determine a 3-D geophysical position of the SDV 502.

Positioning system 151 may also use, either alone or in conjunction with a GPS system, physical movement sensors such as accelerometers (which measure rates of changes to a vehicle in any direction), speedometers (which measure the instantaneous speed of a vehicle), airflow meters (which measure the flow of air around a vehicle), etc. Such physical movement sensors may incorporate the use of semiconductor strain gauges, electromechanical gauges that take readings from drivetrain rotations, barometric sensors, etc.

With respect to the feature of 2) sensing other cars and/or obstacles and/or physical structures around SDV 502, the positioning system 151 may use radar or other electromagnetic energy that is emitted from an electromagnetic radiation transmitter (e.g., transceiver 523 shown in FIG. 5), bounced off a physical structure (e.g., another car), and then received by an electromagnetic radiation receiver (e.g., the same transceiver 523 that emitted the electromagnetic radiation). An exemplary positioning system within SDV 502 is a Light Detection and Ranging (LIDAR) (e.g., the depicted LIDAR 533) or Laser Detection and Ranging (LADAR) system that measures the time it takes to receive back the emitted electromagnetic radiation (e.g., light), and/or evaluate a Doppler shift (i.e., a change in frequency to the electromagnetic radiation that is caused by the relative movement of the SDV 502 to objects being interrogated by the electromagnetic radiation) in the received electromagnetic radiation from when it was transmitted, the presence and location of other physical objects can be ascertained by the SDV on-board computer 501.

With respect to the feature of 3) measuring the speed and direction of the SDV 502, this can be accomplished by taking readings from an on-board speedometer (not depicted) on the SDV 502 and/or detecting movements to the steering mechanism (also not depicted) on the SDV 502 and/or the positioning system 151 discussed above.

With respect to the feature of 4) providing any other inputs needed to safely control the movement of the SDV 502, such inputs include, but are not limited to, control signals to activate a horn, turning indicators, flashing emergency lights, etc. on the SDV 502.

In one or more embodiments of the present invention, SDV 502 includes roadway sensors 511 that are coupled to the SDV 502. Roadway sensors 511 may include sensors that are able to detect the amount of water, snow, ice, etc. on a roadway (e.g., using cameras, heat sensors, moisture sensors, thermometers, etc.). Roadway sensors 511 also include sensors that are able to detect "rough" roadways (e.g., roadways having potholes, poorly maintained pavement, no paving, etc.) using cameras, vibration sensors, etc. Roadway sensors 511 may also include sensors that are also able to detect how dark the roadway is using light sensors.

Similarly, a dedicated camera 521 can be trained on an area around SDV 502, in order to recognize current weather conditions, roadway conditions, etc. around the SDV 502.

In one or more embodiments of the present invention, also within the SDV 502 are SDV equipment sensors 515. SDV equipment sensors 515 may include cameras aimed at tires on the SDV 502 to detect how much tread is left on the tire. SDV equipment sensors 515 may include electronic sensors that detect how much padding is left of brake calipers on disk brakes. SDV equipment sensors 515 may include drivetrain sensors that detect operating conditions within an engine (e.g., power, speed, revolutions per minute—RPMs of the engine, timing, cylinder compression, coolant levels, engine temperature, oil pressure, etc.), the transmission (e.g., transmission fluid level, conditions of the clutch, gears, etc.), etc. SDV equipment sensors 515 may include sensors that detect the condition of other components of the SDV 502, including lights (e.g., using circuitry that detects if a bulb is broken), wipers (e.g., using circuitry that detects a faulty wiper blade, wiper motor, etc.), etc. Readings from SDV equipment sensors 515 can be used to modify the proposed route for SDV 502. For example, if the SDV equipment sensors 515 detect that the brake linings on SDV 502 are badly worn, and roadway 305 shown in FIG. 3 has a steep downhill grade, and roadway 307 shown in FIG. 3 is flat, then vehicle support system 201 may direct SDV 502 to take alternate roadway 307.

In one or more embodiments of the present invention, also within SDV 502 is a telecommunication device 525, which is able to send messages to a telecommunication device (e.g., when vehicle-based transceiver 523 is operating on a cellular network).

In one or more embodiments of the present invention, SDV 502 also includes SDV physical configuration mechanisms 507, which are under the control of the SDV on-board computer 501. Examples of SDV physical configuration mechanisms 507 are mechanisms that control seating configurations, doors being opened, trunks being opened, etc.

As discussed above, autonomous vehicles are capable of controlling their own movement automatically. Autonomous vehicles can also receive commands from a central controller (e.g., vehicle support system 201 shown in FIG. 2), which may be a cloud server (i.e., a real or virtual server than is available via a wide area network). As such, the present invention enables the system to control many autonomous vehicles (e.g., SDVs) remotely with a graphical user interface (GUI) based approach, so that a single operator or team of operators can control numerous autonomous vehicles in an efficient manner.

Thus, in one or more embodiments of the present invention, the passenger vehicle (e.g., passenger vehicle 202 shown in FIG. 2) is a self-driving vehicle (e.g., SDV 502 shown in FIG. 5). In this embodiment, the method further includes transmitting, by one or more processors, the directions for the travel route to a self-driving vehicle on-board computer (e.g., SDV on-board computer 501 shown in FIG. 5), where the self-driving vehicle on-board computer controls all operations of the self-driving vehicle, and where the directions transmitted to the self-driving vehicle on-board computer cause the self-driving vehicle to autonomously take the travel route created by the vehicle support system 201 to the desired destination.

The present invention may be implemented in one or more embodiments using cloud computing. Nonetheless, it is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 6:
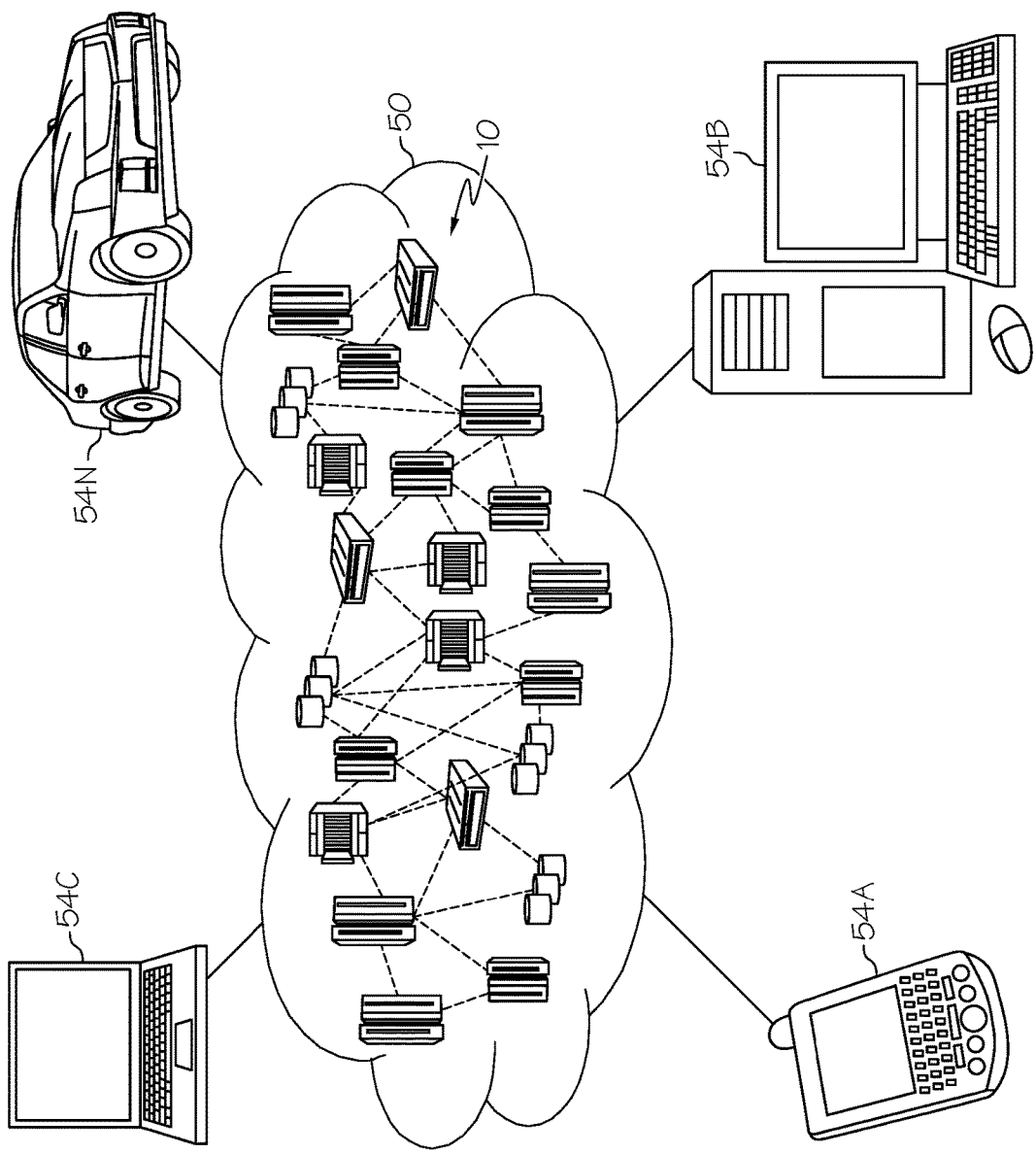
FIG. 6 depicts a cloud computing node according to an embodiment of the present disclosure.

Referring now to FIG. 6, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-54N shown in FIG. 6 are intended to be illustrative only and that computing nodes 10 and cloud computing environment 50 can communicate with any type of computerized device over any type of network and/or network addressable connection (e.g., using a web browser).

Figure 7:
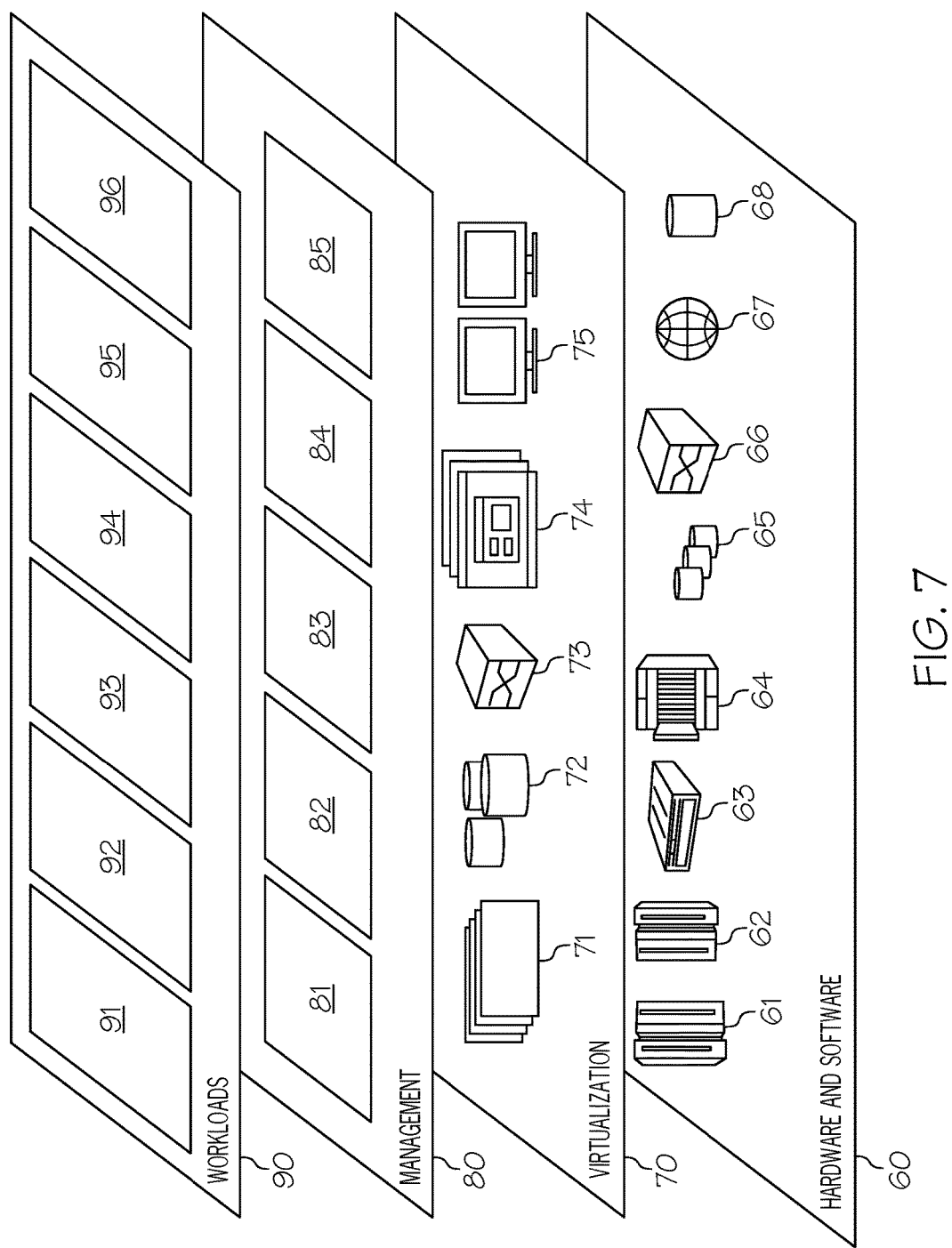
FIG. 7 depicts abstraction model layers according to an embodiment of the present disclosure.

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and passenger vehicle control processing 96, which performs logical processing used to implement one or more embodiments of the present invention as described herein.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of various embodiments of the present invention has been presented for purposes of illustration and description, but is not intended to be exhaustive or limited to the present invention in the form disclosed. Many modifications and variations will be apparent to those of ordinary skill in the art without departing from the scope and spirit of the present invention. The embodiment was chosen and described in order to best explain the principles of the present invention and the practical application, and to enable others of ordinary skill in the art to understand the present invention for various embodiments with various modifications as are suited to the particular use contemplated.

Any methods described in the present disclosure may be implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, any software-implemented method described herein may be emulated by a hardware-based VHDL program, which is then applied to a VHDL chip, such as a FPGA.

Having thus described embodiments of the present invention of the present application in detail and by reference to illustrative embodiments thereof, it will be apparent that modifications and variations are possible without departing from the scope of the present invention defined in the appended claims.

What is claimed is:

1. A method comprising:
   identifying, by one or more processors, an occupant of a passenger vehicle;
   receiving, by one or more processors, biometric sensor readings from a biometric sensor that is monitoring the occupant in real time, wherein the biometric sensor readings indicate a real-time emotional state of the occupant;
   generating, by one or more processors, a personal profile for the occupant of the passenger vehicle based on the biometric sensor readings received from the biometric sensor that is monitoring the occupant in real time;
   receiving, by one or more processors, a desired destination and travel schedule for the occupant of the passenger vehicle;
   receiving, by one or more processors, environmental sensor readings indicating a real-time environmental state of the passenger vehicle, wherein the real-time environmental state of the passenger vehicle is from a group of environmental states consisting of current weather conditions and current roadway obstructions for a roadway on which the passenger vehicle is currently traveling;
   creating, by one or more processors, a travel route for the passenger vehicle based on the biometric sensor readings, the personal profile for the occupant of the passenger vehicle, the desired destination and travel schedule, and the real-time environmental state of the passenger vehicle; and
   transmitting to the passenger vehicle, by one or more processors, directions for the travel route.

2. The method of claim 1, wherein the desired destination is for an appointment for the occupant, and wherein the method further comprises:
   receiving, by one or more processors, an indication of an importance level of the appointment for the occupant; and
   adjusting, by one or more processors, the travel route based on the importance level of the appointment for the occupant.

3. The method of claim 1, further comprising:
   adjusting, by one or more processors, the travel route based on biometric sensor readings for other occupants of the passenger vehicle.

4. The method of claim 1, where the occupant is a driver of the passenger vehicle, and wherein the method further comprises:
   retrieving, by one or more processors, a driver profile for the driver of the passenger vehicle;
   adjusting, by one or more processors, the personal profile based on the retrieved driver profile to create an adjusted personal profile; and
   adjusting, by one or more processors, the travel route based on the adjusted personal profile of the driver of the passenger vehicle.

5. The method of claim 1, wherein the passenger vehicle is a self-driving vehicle, and wherein the method further comprises:
   transmitting, by one or more processors, the directions for the travel route to a self-driving vehicle on-board computer, wherein the self-driving vehicle on-board computer controls all operations of the self-driving vehicle, and wherein the directions transmitted to the self-driving vehicle on-board computer cause the self-driving vehicle to autonomously take the travel route to the desired destination.

6. The method of claim 1, further comprising:
   receiving, by one or more processors, updated biometric sensor readings for the occupant while the passenger vehicle is traveling along the travel route; and modifying, by one or more processors, the travel route based on the updated biometric sensor readings.

7. The method of claim 1, further comprising:
transmitting, by one or more processors, multiple alternative routes to the occupant of the passenger vehicle.

8. A computer program product comprising one or more computer readable storage mediums, and program instructions stored on at least one of the one or more storage mediums, the stored program instructions comprising:
program instructions to identify an occupant of a passenger vehicle;
program instructions to receive biometric sensor readings from a biometric sensor that is monitoring the occupant in real time, wherein the biometric sensor readings indicate a real-time emotional state of the occupant;
program instructions to generate a personal profile for the occupant of the passenger vehicle based on the biometric sensor readings received from the biometric sensor that is monitoring the occupant in real time;
program instructions to receive a desired destination and travel schedule for the occupant of the passenger vehicle;
program instructions to receive environmental sensor readings indicating a real-time environmental state of the passenger vehicle, wherein the real-time environmental state of the passenger vehicle is from a group of environmental states consisting of current weather conditions and current roadway obstructions for a roadway on which the passenger vehicle is currently traveling;
program instructions to create a travel route for the passenger vehicle based on the biometric sensor readings, the personal profile for the occupant of the passenger vehicle, the desired destination and travel schedule, and the real-time environmental state of the passenger vehicle; and
program instructions to transmit, to the passenger vehicle, directions for the travel route.

9. The computer program product of claim 8, wherein the desired destination is for an appointment for the occupant, and wherein the computer program product further comprises:
program instructions to receive an indication of an importance level of the appointment for the occupant; and
program instructions to adjust the travel route based on the importance level of the appointment for the occupant.

10. The computer program product of claim 8, further comprising:
program instructions to adjust the travel route based on biometric sensor readings for other occupants of the passenger vehicle.

11. The computer program product of claim 8, where the occupant is a driver of the passenger vehicle, and wherein the computer program product further comprises:
program instructions to retrieve a driver profile for the driver of the passenger vehicle;
program instructions to adjust the personal profile based on the retrieved driver profile to create an adjusted personal profile; and
program instructions to adjust the travel route based on the adjusted personal profile of the driver of the passenger vehicle.

12. The computer program product of claim 8, wherein the passenger vehicle is a self-driving vehicle, and wherein the computer program product further comprises:
program instructions to transmit the directions for the travel route to a self-driving vehicle on-board computer, wherein the self-driving vehicle on-board computer controls all operations of the self-driving vehicle, and wherein the directions transmitted to the self-driving vehicle on-board computer cause the self-driving vehicle to autonomously take the travel route to the desired destination.

13. The computer program product of claim 8, further comprising:
program instructions to receive updated biometric sensor readings for the occupant while the passenger vehicle is traveling along the travel route; and
program instructions to modify the travel route based on the updated biometric sensor readings.

14. The computer program product of claim 8, further comprising:
program instructions to transmit multiple alternative routes to the occupant of the passenger vehicle.

15. A computer system comprising one or more processors, one or more computer readable memories, and one or more computer readable storage mediums, and program instructions stored on at least one of the one or more storage mediums for execution by at least one of the one or more processors via at least one of the one or more memories, the stored program instructions comprising:
program instructions to identify an occupant of a passenger vehicle;
program instructions to receive biometric sensor readings from a biometric sensor that is monitoring the occupant in real time, wherein the biometric sensor readings indicate a real-time emotional state of the occupant;
program instructions to generate a personal profile for the occupant of the passenger vehicle based on the biometric sensor readings received from the biometric sensor that is monitoring the occupant in real time;
program instructions to receive a desired destination and travel schedule for the occupant of the passenger vehicle;
program instructions to receive environmental sensor readings indicating a real-time environmental state of the passenger vehicle, wherein the real-time environmental state of the passenger vehicle is from a group of environmental states consisting of current weather conditions and current roadway obstructions for a roadway on which the passenger vehicle is currently traveling;
program instructions to create a travel route for the passenger vehicle based on the biometric sensor readings, the personal profile for the occupant of the passenger vehicle, the desired destination and travel schedule, and the real-time environmental state of the passenger vehicle; and
program instructions to transmit, to the passenger vehicle, directions for the travel route.

16. The computer system of claim 15, wherein the desired destination is for an appointment for the occupant, and wherein the computer system further comprises:
program instructions to receive an indication of an importance level of the appointment for the occupant; and
program instructions to adjust the travel route based on the importance level of the appointment for the occupant.

17. The computer system of claim 15, further comprising:
program instructions to adjust the travel route based on biometric sensor readings for other occupants of the passenger vehicle.

18. The computer system of claim 15, where the occupant is a driver of the passenger vehicle, and wherein the computer program product further comprises:

program instructions to retrieve a driver profile for the driver of the passenger vehicle;

program instructions to adjust the personal profile based on the retrieved driver profile to create an adjusted personal profile; and program instructions to adjust the travel route based on the adjusted personal profile of the driver of the passenger vehicle.

19. The computer system of claim 15, wherein the passenger vehicle is a self-driving vehicle, and wherein the computer system further comprises:

program instructions to transmit the directions for the travel route to a self-driving vehicle on-board computer, wherein the self-driving vehicle on-board computer controls all operations of the self-driving vehicle, and wherein the directions transmitted to the self-driving vehicle on-board computer cause the self-driving vehicle to autonomously take the travel route to the desired destination.

20. The computer system of claim 15, further comprising:

program instructions to receive updated biometric sensor readings for the occupant while the passenger vehicle is traveling along the travel route; and program instructions to modify the travel route based on the updated biometric sensor readings.

\* \* \* \* \*